US009572335B2

(12) United States Patent
Bailey

(10) Patent No.: US 9,572,335 B2
(45) Date of Patent: Feb. 21, 2017

(54) VIDEO RECORDING SYSTEM AND METHODS

(71) Applicant: Navico Holding AS, Egersund (NO)

(72) Inventor: Paul Robert Bailey, Auckland (NZ)

(73) Assignee: NAVICO HOLDING AS, Egersund (NO)

(*) Notice: Subject to any disclaimer, the term of this patent is extended or adjusted under 35 U.S.C. 154(b) by 106 days.

(21) Appl. No.: 14/259,052

(22) Filed: Apr. 22, 2014

(65) Prior Publication Data

US 2015/0055930 A1 Feb. 26, 2015

Related U.S. Application Data

(60) Provisional application No. 61/868,444, filed on Aug. 21, 2013.

(51) Int. Cl.
*H04N 5/91* (2006.01)
*H04N 5/232* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01);
(Continued)

(58) Field of Classification Search
CPC ........ A01K 97/00; A01K 99/00; A01K 79/00; G01C 21/203; G01C 21/20; H04Q 9/00; G06F 11/3438; G06F 11/3476; G06F 17/30867; G06F 3/017; G06F 3/00; G06K 9/00342; G01B 21/00; G11B 27/031; G06T 7/2093; H04N 5/232; H04N 5/91; H04N 21/4335
(Continued)

(56) References Cited

U.S. PATENT DOCUMENTS 4,829,493 A 5/1989 Bailey
4,879,697 A 11/1989 Lowrance et al.
(Continued)

FOREIGN PATENT DOCUMENTS

DE 102004059619 A1 6/2006
EP 1 561 377 A1 8/2005
(Continued)

OTHER PUBLICATIONS

Allen, et al.; Upper Extremity Kinematic Trends of Fly-Casting; Establishing the Effects of Line Length; Sports Biomechanics; vol. 7, No. 1; Jan. 1, 2008; pp. 38-53.
(Continued)

*Primary Examiner* — Gelek W Topgyal
(74) *Attorney, Agent, or Firm* — Nelson Mullins Riley & Scarborough LLP

(57) ABSTRACT

A non-transitory computer-readable medium having stored thereon computer-executable instructions which, when executed by a computer, cause the computer to receive a first notification that a first cast has been made. The computer-executable instructions may further include instructions, which cause the computer to receive data regarding a video input. The computer-executable instructions may further include instructions, which cause the computer to receive a second notification that a second cast has been made. The computer-executable instructions may further include instructions, which cause the computer to delete a portion of the data regarding the video input that is associated with the first cast in response to receiving the second notification.

20 Claims, 7 Drawing Sheets

(51) Int. Cl.

| | | |
|---|---|---|
| A01K 97/00 | (2006.01) | |
| G11B 27/034 | (2006.01) | |
| G11B 27/17 | (2006.01) | |
| G11B 31/00 | (2006.01) | |
| A01K 99/00 | (2006.01) | |
| A01K 79/00 | (2006.01) | |
| G11B 27/28 | (2006.01) | |
| G11B 27/34 | (2006.01) | |
| G08C 17/02 | (2006.01) | |
| G06F 3/01 | (2006.01) | |
| G06T 11/20 | (2006.01) | |
| G06T 7/20 | (2006.01) | |
| G06T 7/60 | (2006.01) | |
| G01C 21/20 | (2006.01) | |
| A61B 5/11 | (2006.01) | |
| G01B 21/00 | (2006.01) | |
| G06Q 10/00 | (2012.01) | |
| G06Q 50/00 | (2012.01) | |
| H04N 21/4335 | (2011.01) | |
| G06F 3/023 | (2006.01) | |
| G06F 15/02 | (2006.01) | |
| G11B 27/031 | (2006.01) | |
| G06F 17/30 | (2006.01) | |
| G06F 11/34 | (2006.01) | |
| G06K 9/00 | (2006.01) | |
| G06F 3/0346 | (2013.01) | |
| H04Q 9/00 | (2006.01) | |
| G06F 3/02 | (2006.01) | |
| G06F 13/30 | (2006.01) | |
| B63B 49/00 | (2006.01) | |
| G01S 15/96 | (2006.01) | |
| G06F 11/30 | (2006.01) | |
| G01S 7/00 | (2006.01) | |

(52) U.S. Cl.
CPC ............. *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01); *G06F 3/0231* (2013.01); *G06F 3/0346* (2013.01); *G06F 11/3438* (2013.01); *G06F 11/3476* (2013.01); *G06F 15/0225* (2013.01); *G06F 17/30867* (2013.01); *G06K 9/00342* (2013.01); *G06Q 10/00* (2013.01); *G06Q 50/01* (2013.01); *G06T 7/2033* (2013.01); *G06T 7/2093* (2013.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02B 60/165* (2013.01)

(58) Field of Classification Search
USPC ........ 386/224, 248, 278, 295; 43/4; 345/156
See application file for complete search history.

(56) References Cited

U.S. PATENT DOCUMENTS

| | | |
|---|---|---|
| 5,025,423 A | 6/1991 | Earp |
| 5,191,341 A | 3/1993 | Gouard et al. |
| 5,321,391 A | 6/1994 | Fox |
| 5,446,775 A * | 8/1995 | Wright ............... A61B 5/11 377/23 |
| 5,537,380 A | 7/1996 | Sprankle, Jr. et al. |
| 5,546,695 A | 8/1996 | Langer |
| 6,222,449 B1 | 4/2001 | Twining |
| 6,225,984 B1 | 5/2001 | Crawford |
| 6,252,544 B1 | 6/2001 | Hoffberg |
| 6,263,147 B1 | 7/2001 | Tognazzini |
| 6,321,158 B1 | 11/2001 | DeLorme et al. |
| 6,411,283 B1 | 6/2002 | Murphy |
| 6,418,080 B2 | 7/2002 | Inouchi |
| 6,421,299 B1 | 7/2002 | Betts et al. |
| 6,459,372 B1 | 10/2002 | Branham et al. |
| 6,567,792 B1 | 5/2003 | Arnold |
| 6,584,722 B1 * | 7/2003 | Walls ............... A01K 97/00 377/5 |
| 6,587,740 B2 | 7/2003 | Byrne et al. |
| 6,751,626 B2 | 6/2004 | Brown et al. |
| 6,761,692 B2 | 7/2004 | Angelsen et al. |
| 6,798,378 B1 | 9/2004 | Walters |
| 6,816,782 B1 | 11/2004 | Walters et al. |
| 7,002,579 B2 | 2/2006 | Olson |
| 7,236,426 B2 | 6/2007 | Turner et al. |
| 7,243,457 B1 | 7/2007 | Smith et al. |
| 7,319,992 B2 | 1/2008 | Gaos |
| 7,321,824 B1 | 1/2008 | Nesbitt |
| 7,430,461 B1 | 9/2008 | Michaels |
| 7,652,952 B2 | 1/2010 | Betts et al. |
| 7,710,825 B2 | 5/2010 | Betts et al. |
| 7,722,218 B2 | 5/2010 | Leung |
| 7,729,203 B2 | 6/2010 | Betts et al. |
| 7,755,974 B2 | 7/2010 | Betts et al. |
| 7,812,667 B2 | 10/2010 | Fagg |
| 7,870,496 B1 | 1/2011 | Sherwani |
| 7,890,867 B1 | 2/2011 | Margulis |
| 8,019,532 B2 | 9/2011 | Sheha et al. |
| 8,040,758 B1 | 10/2011 | Dickinson |
| 8,063,540 B2 | 11/2011 | Angelsen et al. |
| 8,452,797 B1 | 5/2013 | Paleja et al. |
| 8,468,164 B1 | 6/2013 | Paleja et al. |
| 2001/0054961 A1 | 12/2001 | Twining |
| 2002/0035574 A1 | 3/2002 | Dumas |
| 2002/0093541 A1 | 7/2002 | Schileru-Key |
| 2002/0099457 A1 | 7/2002 | Fredlund et al. |
| 2002/0116421 A1 | 8/2002 | Fox et al. |
| 2003/0046689 A1 | 3/2003 | Gaos |
| 2003/0056419 A1 | 3/2003 | Squires et al. |
| 2003/0089020 A1 | 5/2003 | Dirito |
| 2004/0124297 A1 | 7/2004 | Steer |
| 2004/0162830 A1 | 8/2004 | Shirwadkar et al. |
| 2004/0193364 A1 | 9/2004 | Chojnacki |
| 2004/0249860 A1 | 12/2004 | Stechschulte et al. |
| 2005/0037872 A1 | 2/2005 | Fredlund et al. |
| 2005/0102101 A1 | 5/2005 | Beesley et al. |
| 2006/0013066 A1 | 1/2006 | Nishimori et al. |
| 2006/0048434 A1 | 3/2006 | Congel |
| 2006/0119585 A1 | 6/2006 | Skinner |
| 2006/0224940 A1 | 10/2006 | Lee |
| 2006/0265931 A1 | 11/2006 | McFadden et al. |
| 2007/0011334 A1 | 1/2007 | Higgins et al. |
| 2007/0045010 A1 | 3/2007 | Kasperek |
| 2007/0058489 A1 | 3/2007 | Bratcher |
| 2007/0220798 A1 | 9/2007 | Davidson |
| 2008/0126935 A1 | 5/2008 | Blomgren |
| 2008/0165022 A1 | 7/2008 | Herz et al. |
| 2008/0204424 A1 | 8/2008 | Jin et al. |
| 2008/0246627 A1 | 10/2008 | Guazzelli |
| 2009/0064055 A1 | 3/2009 | Chaudhri et al. |
| 2009/0099871 A1 | 4/2009 | Gadodia |
| 2009/0105952 A1 | 4/2009 | Grace et al. |
| 2009/0179789 A1 | 7/2009 | Haughay, Jr. et al. |
| 2009/0240354 A1 | 9/2009 | Davidson |

(56) References Cited

U.S. PATENT DOCUMENTS

| | | | |
|---|---|---|---|
| 2009/0241636 A1* | 10/2009 | Obori | A63F 13/06 73/12.04 |
| 2009/0249247 A1 | 10/2009 | Tseng et al. | |
| 2009/0258710 A1 | 10/2009 | Quatrochi | |
| 2009/0271054 A1 | 10/2009 | Dokken | |
| 2009/0287409 A1 | 11/2009 | Summers | |
| 2009/0295626 A1 | 12/2009 | Su | |
| 2010/0049468 A1 | 2/2010 | Papadourakis | |
| 2010/0080082 A1 | 4/2010 | Betts et al. | |
| 2010/0145601 A1 | 6/2010 | Kurtti et al. | |
| 2010/0199225 A1 | 8/2010 | Coleman et al. | |
| 2010/0226203 A1 | 9/2010 | Buttle et al. | |
| 2010/0250122 A1 | 9/2010 | Kubota et al. | |
| 2010/0319235 A1 | 12/2010 | Panaro | |
| 2011/0007035 A1 | 1/2011 | Shai | |
| 2011/0013484 A1 | 1/2011 | Coleman et al. | |
| 2011/0013485 A1 | 1/2011 | Maguire | |
| 2011/0019887 A1 | 1/2011 | Roehrig et al. | |
| 2011/0025720 A1 | 2/2011 | Jo et al. | |
| 2011/0067290 A1 | 3/2011 | Miskatovic | |
| 2011/0082644 A1 | 4/2011 | Imasaka et al. | |
| 2011/0154183 A1 | 6/2011 | Burns et al. | |
| 2011/0208479 A1 | 8/2011 | Chaves | |
| 2011/0213515 A1 | 9/2011 | Haymart et al. | |
| 2011/0214500 A1* | 9/2011 | Cabrera | G01C 13/00 73/170.29 |
| 2011/0257819 A1 | 10/2011 | Chen et al. | |
| 2012/0001773 A1 | 1/2012 | Lyons et al. | |
| 2012/0011437 A1 | 1/2012 | James et al. | |
| 2012/0014220 A1 | 1/2012 | Depasqua | |
| 2012/0047790 A1* | 3/2012 | Hess | A01K 85/16 43/42 |
| 2012/0069712 A1 | 3/2012 | Potanin et al. | |
| 2012/0106300 A1 | 5/2012 | Maguire | |
| 2012/0144384 A1 | 6/2012 | Baek | |
| 2012/0144723 A1* | 6/2012 | Davidson | A01K 85/01 43/17.6 |
| 2012/0185801 A1 | 7/2012 | Madonna et al. | |
| 2012/0316456 A1 | 12/2012 | Rahman et al. | |
| 2012/0316458 A1 | 12/2012 | Rahman et al. | |
| 2012/0317167 A1 | 12/2012 | Rahman et al. | |
| 2013/0007665 A1 | 1/2013 | Chaudhri et al. | |
| 2013/0040714 A1 | 2/2013 | Rosing | |
| 2013/0074051 A1 | 3/2013 | Freeman | |
| 2013/0096575 A1 | 4/2013 | Olson | |
| 2013/0107031 A1* | 5/2013 | Atkinson | H04N 1/00347 348/81 |
| 2013/0281087 A1 | 10/2013 | Ruhanen et al. | |
| 2013/0307720 A1 | 11/2013 | Lilburn | |
| 2013/0343151 A1 | 12/2013 | Shiraki et al. | |
| 2014/0012587 A1 | 1/2014 | Park | |
| 2014/0032468 A1 | 1/2014 | Anandaraj | |
| 2014/0071059 A1 | 3/2014 | Girault | |
| 2014/0111368 A1 | 4/2014 | Lee et al. | |
| 2014/0180566 A1 | 6/2014 | Malhotra | |
| 2014/0195297 A1 | 7/2014 | Abuelsaad et al. | |
| 2014/0358483 A1* | 12/2014 | da Rosa | A01K 97/00 702/188 |
| 2015/0019135 A1 | 1/2015 | Kacyvenski | |
| 2015/0051786 A1 | 2/2015 | Wang | |
| 2015/0054655 A1 | 2/2015 | Bailey | |
| 2015/0054732 A1 | 2/2015 | Bailey | |
| 2015/0054828 A1 | 2/2015 | Bailey | |
| 2015/0054829 A1 | 2/2015 | Bailey | |
| 2015/0055827 A1 | 2/2015 | Bailey | |
| 2015/0055930 A1 | 2/2015 | Bailey | |
| 2015/0057929 A1 | 2/2015 | Bailey | |
| 2015/0057965 A1 | 2/2015 | Gaynor | |
| 2015/0057968 A1 | 2/2015 | Bailey | |
| 2015/0058020 A1 | 2/2015 | Bailey | |
| 2015/0058237 A1* | 2/2015 | Bailey | G08C 17/02 705/319 |
| 2015/0058323 A1 | 2/2015 | Bailey | |
| 2015/0310524 A1 | 10/2015 | Gospodarek et al. | |
| 2016/0125348 A1 | 5/2016 | Dyer et al. | |

FOREIGN PATENT DOCUMENTS

| | | |
|---|---|---|
| EP | 2 613 223 A1 | 7/2013 |
| JP | 2004 207812 A | 7/2004 |
| JP | 2006 158239 A | 6/2006 |
| JP | 2010 193284 A | 9/2010 |
| JP | 2011 139647 A | 7/2011 |
| WO | 98/02037 A1 | 1/1998 |
| WO | 2004/088572 | 10/2004 |
| WO | 2010/056392 | 5/2010 |
| WO | 2012/170163 | 12/2012 |
| WO | 2014/088508 A1 | 6/2014 |
| ZA | 200 308 052 A | 7/2004 |

OTHER PUBLICATIONS

First look at new Mio Link Ant +/Bluetooth Smart optical heart rate wrist band; http://www.dcrainmaker.com/2014/01/mio-link-first-look.html; Jan. 6, 2014 (accessed Apr. 18, 2016).

SAS, "SAS BI Dashboard 4.31 User's Guide", Second Edition, by SAS Electronic book, Aug. 1, 2012, downloaded at http://support.sas.com/documentation/cdl/en/bidbrdrug/65580/PDF/default/bidrdrug.pdf.

PCT International Search Report and Written Opinion; PCT/IB2013/060285, dated Feb. 18, 2014.

PCT International Search Report and Written Opinion; PCT/IB2014/063974, dated Dec. 2, 2014.

PCT International Search Report and Written Opinion; PCT/IB2014/063975, dated Dec. 3, 2014.

PCT International Search Report and Written Opinion; PCT/IB2014/063976, dated Dec. 12, 2014.

PCT International Search Report and Written Opinion; PCT/IB2014/063979, dated Jan. 7, 2015.

PCT International Search Report and Written Opinion; PCT/IB2014/063980, dated Jan. 5, 2015.

PCT International Search Report and Written Opinion; PCT/IB2014/063982, dated Dec. 22, 2014.

PCT International Search Report and Written Opinion; PCT/IB2014/063983, dated Mar. 5, 2015.

PCT International Search Report and Written Opinion; PCT/US2013/047645, dated Sep. 27, 2013.

PCT International Search Report and Written Opinion; PCT/US2013/047869, dated Oct. 21, 2013.

PCT International Search Report and Written Opinion; PCT/US2013/047926, dated Oct. 11, 2013.

PCT International Search Report and Written Opinion; PCT/US2013/048129, dated Oct. 17, 2013.

PCT International Search Report and Written Opinion; PCT/US2013/048177, dated Oct. 21, 2013.

PCT International Search Report and Written Opinion; PCT/IB2014/063973, dated Nov. 28, 2014.

PCT International Search Report and Written Opinion; PCT/IB2014/063981, dated Feb. 10, 2015.

PCT International Search Report and Written Opinion; PCT/IB2014/063978, dated Dec. 19, 2014.

PCT International Search Report and Written Opinion; PCT/IB2014/063977, dated Nov. 28, 2014.

McElderry; *At-Sea Observing Using Video-Based Electronic Monitoring*; Prepared for: Electronic Monitoring Workshop Jul. 29-30, 2008; Archipelago Marine Research Ltd.

* cited by examiner

Fishing Motion Detection Software 500

VIDEO RECORDING SYSTEM AND METHODS

CROSS-REFERENCE TO RELATED APPLICATIONS

This application claims the benefit of U.S. Provisional Patent Application Ser. No. 61/868,444, filed Aug. 21, 2013, titled FISHING DATA COLLECTION AND USE, and the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Being able to record a catch during a fishing trip is very useful for memorializing the experience. However, during any fishing trip, there may be time periods when fish do not bite and many casts do not result in caught fishes. Recording the entire fishing trip to capture each catch may result in plenty of video that is of little personal value.

SUMMARY

Described herein are implementations of various technologies for a method. In one implementation, a non-transitory computer-readable medium having stored thereon computer-executable instructions which, when executed by a computer, cause the computer to perform various actions. The actions may include receiving a first notification that a first cast has been made. The actions may include receiving data regarding a video input. The actions may include receiving a second notification that a second cast has been made. The actions may include deleting data regarding the video input that is associated with the first cast in response to receiving the second notification.

In one implementation, the data regarding the video input may be deleted without deleting data regarding the video input that is associated with the second cast. In another implementation, the actions may include receiving a first time stamp corresponding to the first cast. The actions may include receiving a second time stamp corresponding to the second cast. The data between the first time stamp and the second time stamp may be the data associated with the first cast that is deleted. In another implementation, the data regarding the video input may be associated with the first cast by indexing the data regarding the video input to data received after the first notification and before the second notification. In another implementation, the data regarding the video input may be data recorded by a video camera. In another implementation, the first notification may be received from a wearable device. In another implementation, the first notification may be received over a wireless connection. In another implementation, the first notification may include motion data corresponding to a fishing cast.

Described herein are implementations of various technologies for a method. In one implementation, a non-transitory computer-readable medium having stored thereon computer-executable instructions which, when executed by a computer, cause the computer to perform various actions. The actions may include receiving a notification that a cast has been made. The actions may include receiving data regarding a video input associated with the cast. The actions may include determining whether a catch has been detected that corresponds to the cast. The actions may include storing the data regarding the video input in response to a determination that a catch has been detected.

In one implementation, the data regarding the video input may be stored in association with the cast or the catch. In another implementation, the actions may include receiving a notification that a catch has been made. In another implementation, the notification is received from a wearable device. In another implementation, the notification is received over a wireless connection. In another implementation, the notification may include motion data corresponding to a fishing cast.

Described herein are implementations of various technologies for a method. In one implementation, a non-transitory computer-readable medium having stored thereon computer-executable instructions which, when executed by a computer, cause the computer to perform various actions. The actions may include receiving a notification that a first cast has been made. The actions may include receiving data regarding a video input. The actions may include receiving a notification that a button has been pressed, wherein the button is associated with a second cast or a catch being made. The actions may include deleting the data regarding the video input that is associated with the catch being made, if the button is associated with the first cast.

In one implementation, the actions may include storing a portion of the data regarding the video input if the button is associated with the catch being made. In another implementation, the button may be a virtual button located in a graphical user display. In another implementation, the button may be located on a wearable device. In another implementation, a portion of the data regarding the video input may be deleted without deleting the data regarding the video input associated with the second cast. In another implementation, the actions may include receiving a time stamp corresponding to the first cast. The actions may also include receiving a second time stamp corresponding to the button being pressed. The portion of the data being deleted may be the data between the first time stamp and the second time stamp.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

Figure 1:
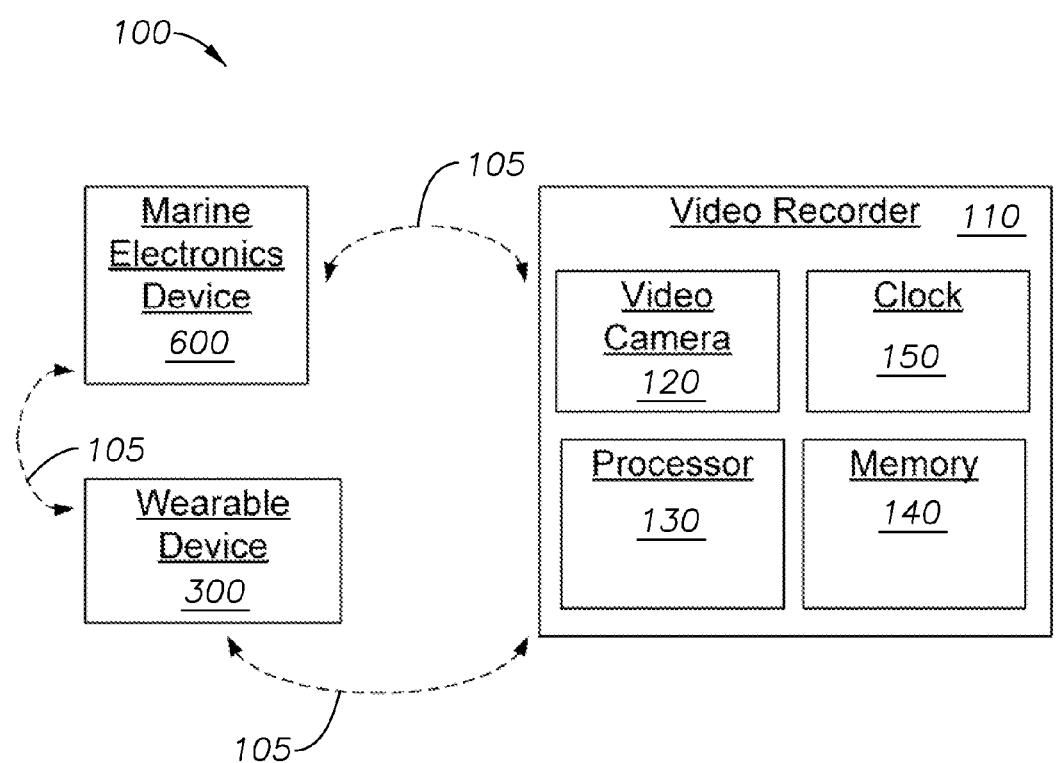
FIG. 1 illustrates a block diagram of a video recording system in accordance with implementations of various techniques described herein.

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of a video recording system described herein will now be described in more detail with reference to FIGS. 1-8.

FIG. 1 illustrates a block diagram of a video recording system 100 in accordance with implementations of various techniques described herein. The video recording system 100 may include several components, such as a wearable device 300, a marine electronics device 600 and a video recorder 110 having a video camera 120, a processor 130, memory 140 and a clock 150. For more information regarding the wearable device 300, see the section titled WEARABLE DEVICE FOR FISHING below. For more information regarding the marine electronics device 600, see the section titled MARINE ELECTRONICS DEVICE below. The video recording system 100 may communicate over wireless or wired network connections 105. The various components of the video recording system 100 are described in more detail with reference to the computing system diagram in FIG. 7.

The video recorder 110 may be a stand-alone unit or embedded in a marine vessel. While one video camera is shown in FIG. 1, more than one video camera may be included in the video recording system 100. In one implementation, the video recorder 110 may record continuously throughout a fishing trip. Data not associated with catches may be deleted afterwards using method 200 below.

The video recording system 100 may record a fisherman throughout a cast. As such, the video recording system 100 may record the casting of a line into the water and when a fisherman catches a fish or anything else resulting from the cast. The video recording system 100 may be configured to detect when a cast, catch or other predetermined event occurs, and limit video recording to time periods associated with those events. For more information regarding cast or catch detection, see the section titled FISHING MOTION DETECTION below. Using the wearable device 300 or the marine electronics device 600, the video recording system 100 may also determine when particular events take place and the video recording system 100 may begin recording or stop recording, accordingly. When nothing is being recorded by the video camera 120, the video recording system may enter a standby mode waiting for a predetermined event to occur to trigger a recording session.

Figure 2:
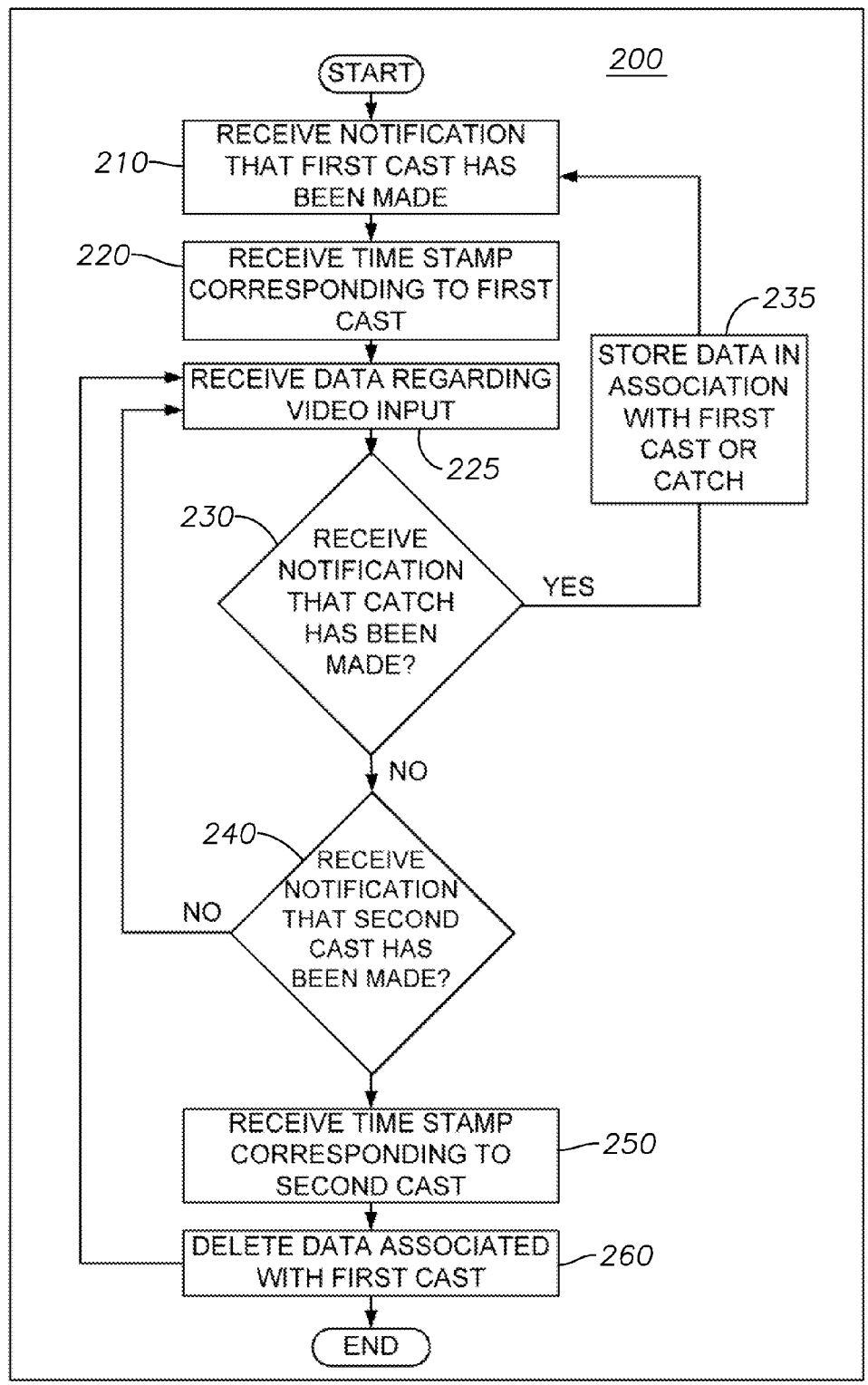
FIG. 2 is a flow diagram of a video recording method in accordance with implementations of various techniques described herein.

FIG. 2 illustrates a flow diagram of a video recording method 200 in accordance with implementations of various techniques described herein. In one implementation, method 200 may be performed by one or more components of the video recording system 100, such as the wearable device 100, the marine electronics device 600 and/or the video recorder 110. It should be understood that while method 200 indicates a particular order of execution of operations, in some implementations, certain portions of the operations might be executed in a different order. Further, in some implementations, additional operations or steps may be added to the method 200. Likewise, some operations or steps may be omitted.

At block 210, the video recording system 100 may receive a notification that a first cast has been made. The notification may be a message sent by the wearable device 100, the marine electronics device 600 or other computer device capable of determining whether a cast has been made. The notification may also be motion data or other sensor data that the video recording system 100 may determine to represent a cast. For more information on using motion data or other sensor data to detect a cast, see the section titled FISHING MOTION DETECTION.

At block 220, the video recording system 100 may receive a time stamp corresponding to the first cast from block 210. The time stamp may be determined by a clock 150 or a timer in the video recording system 100. As such, the time stamp may be based on when the video recording system 100 received the notification at block 210. The time stamp may be part of the notification at block 210 or a message sent separate from the notification. The time stamp may also be a particular time (e.g., 5 seconds before or after a cast is detected) designated in relation to the cast.

At block 225, the video recording system 100 may receive data regarding a video input (i.e., "the received data"). For instance, the video input may be an Audio/Video (AV) input, High Definition Multimedia Interface (HDMI) input, S-Video input, Component (YPbPr) video input, Digital Video Interface (DVI) input or the like. The received data may be data received from the video camera 120 or other audio or video capturing device. The received data may include video as well as related data such as audio recordings, the time, date, metadata, video camera settings, or the like. The received data may be associated with the notification of the first cast from block 210, such as through indexing the received data to the notification or first cast. The received data may be stored in memory 140 or to a hard disk.

While the video recording system 100 may begin receiving data regarding a video input upon receiving the notification at block 210, in one implementation, the video recording system 100 may receive data regarding a video input continuously throughout a fishing trip, such as before the notification at block 210 is received. The video recording system 100 may also record data at predetermined time periods. For instance, the video recording system 100 may receive data regarding a video input whenever the video recording system 100 leaves a standby mode even if no notification has been received that a cast has been made.

At block 230, the video recording system 100 may determine whether a catch has been made. The video recording system 100 may receive a notification regarding a catch similar to a notification that a cast has been made as described at block 210. The video recording system 100 may also receive motion or other sensor data from a wearable device 100 for detecting a catch. If a catch is detected, the process may proceed to block 235. Otherwise, the process may proceed to block 240.

At block 235, the video recording system 100 may store the received data regarding the video input in association with the cast or the catch. For instance, the received data may be converted into a video file using a video format, such as MP4, WMV, AVI, etc. If the first cast from block 210 has a particular identifier, such as an identification number based on the date or time, a video file may be stored in association with the same identifier as the cast. If the catch has a particular identifier, the video file may be stored using the same identifier as the catch. The process may return to block 210 where the method 200 may restart the notification count (i.e., the next received notification that a cast has been made may then be the first cast at block 210) or enter a standby mode until another notification is received showing that a new cast has been made.

As mentioned above, if no catch is detected, then the video recording system 100 may determine whether a notification has been received that a second cast has been made at block 240. This notification may be similar to the notification received at block 210. If a second cast is detected, the process may proceed to block 250. If a second cast has not been detected, the process may return to block 225, where the video recording system 100 may continue to receive data regarding the video input.

At block 250, the video recording system 100 may receive a time stamp corresponding to the second cast from block 240. This time stamp may be similar to the time stamp received at block 220.

At block 260, the video recording system 100 may delete a portion or all of the received data that is associated with the first cast (i.e., "the associated data"). The received data may be associated with a particular cast using several methods. In one implementation, the video recording system 100 may use the time stamps received at blocks 220 and 250 to determine the associated data, e.g., the period of time between the time stamp at block 220 and the time stamp at block 250.

In another implementation, portions of the received data at block 225 may be indexed to a particular cast, such as through metadata. When the video recording system 100 receives a notification that a cast has been made, the video recording system 100 may index the data received after the notification to the corresponding cast until the next notification is received by the video recording system 100. When the next notification is received, the process may index the received data following the next notification to the new cast.

In yet another implementation, the video recording system 100 may delete the received data at a staggered point in time. For example, in order to keep received data associated with the second cast, the video recording system 100 may delete the associated data up until a few seconds before the time stamp corresponding to the second cast. This may ensure that none of the received data associated with the second cast is deleted, such as due to a time delay between making the second cast and the video recording system 100 receiving a notification that the second cast was made.

In still another implementation, the associated data may be deleted in response to the notification regarding the second cast at block 240. As such, the video recording system 100 may delete a portion of the received data associated with the first cast without deleting data associated with the second cast.

After block 260, the process may end, enter a standby mode or return to block 225 to receive data regarding a video input that is associated with the second cast.

In another implementation of method 200, the notification at block 210 or block 240 may be a notification that a button has been pressed on the marine electronics device 600, the video recorder 110, or the wearable device 300. The button may be a physical button or a virtual button, such as an icon on the screen 605. As such, the method 200 may be performed similar to the manner described at blocks 210-260, but when a cast or catch is made, a user may press a button to notify the video recording system 100 of the cast or catch, respectively. In another implementation, at block 250, the received data associated with the first cast may also be deleted in response to a notification that a button was pressed. For instance, the wearable device 300 may have a button designated for deleting the received data that is associated with the previous cast.

In another implementation, one or more virtual buttons may be created on the marine electronics device 600 corresponding to the associated data for one or more of previous casts on a trip. A user may delete or store the associated data by pressing the virtual button corresponding to any desired casts accordingly.

Wearable Device for Fishing

Figure 3:
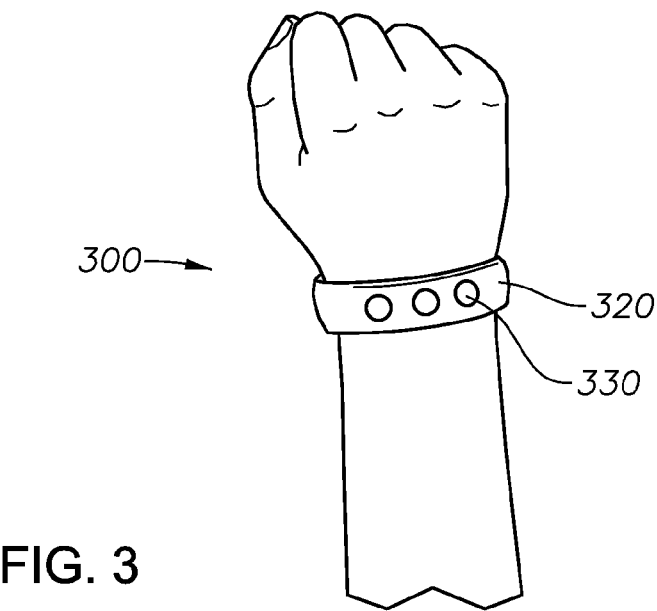
FIG. 3 illustrates a wearable device in accordance with implementations of various techniques described herein.

Fishermen often record details of their fishing trips so that the information can be referenced at a later time, and so that the trip can be analyzed. Using a wearable device that captures motion and determines when a cast has been made, fishing data could easily be recorded by a computer system without the need for significant user input. Accordingly, FIG. 3 illustrates a wearable device 300 in accordance with various implementations described herein. The wearable device 300 may be worn around the fisherman's arm or wrist. The wearable device 300 could also be attached to a fishing rod.

The wearable device 300 may include a housing 320. In one implementation, the housing 320 may be in the shape of a band. The housing 320 may be made of a combination of plastics and rubbers, or of any other synthetic material. The housing 320 may also be waterproof. The housing 320 may include a clasp, or another mechanism to aid in removal of the housing 320 from a user's arm.

Figure 4:
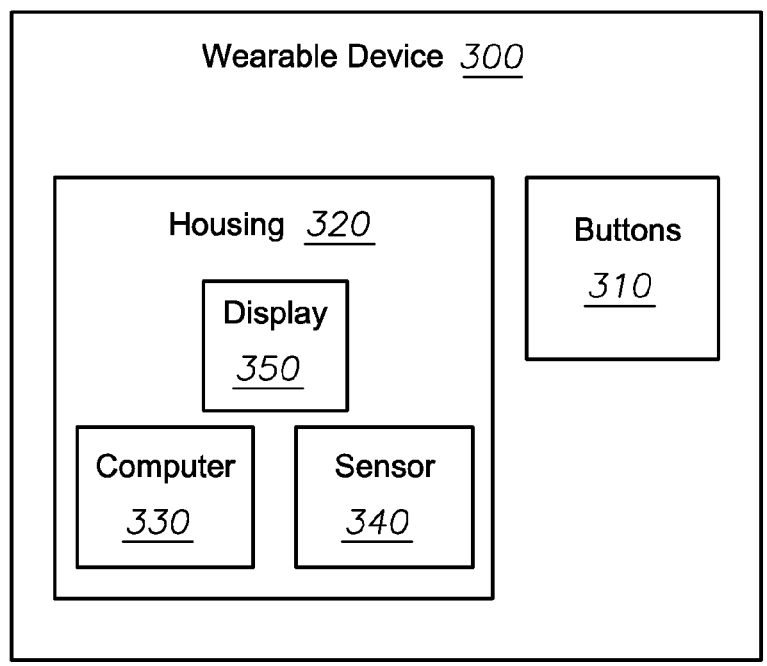
FIG. 4 is a block diagram of a wearable device in accordance with implementations of various techniques described herein.

FIG. 4 illustrates a block diagram of the wearable device 300 in accordance with various implementations described herein. As shown in FIG. 4, the housing 320 may include a computer 330 and at least one motion sensor 340. The at least one motion sensor 340 may include one or more accelerometers, gyroscopes, muscle activity sensors, any other motion sensor, or any combination of motion sensors. The at least one motion sensor 340 is configured to capture motion data.

Figure 7:
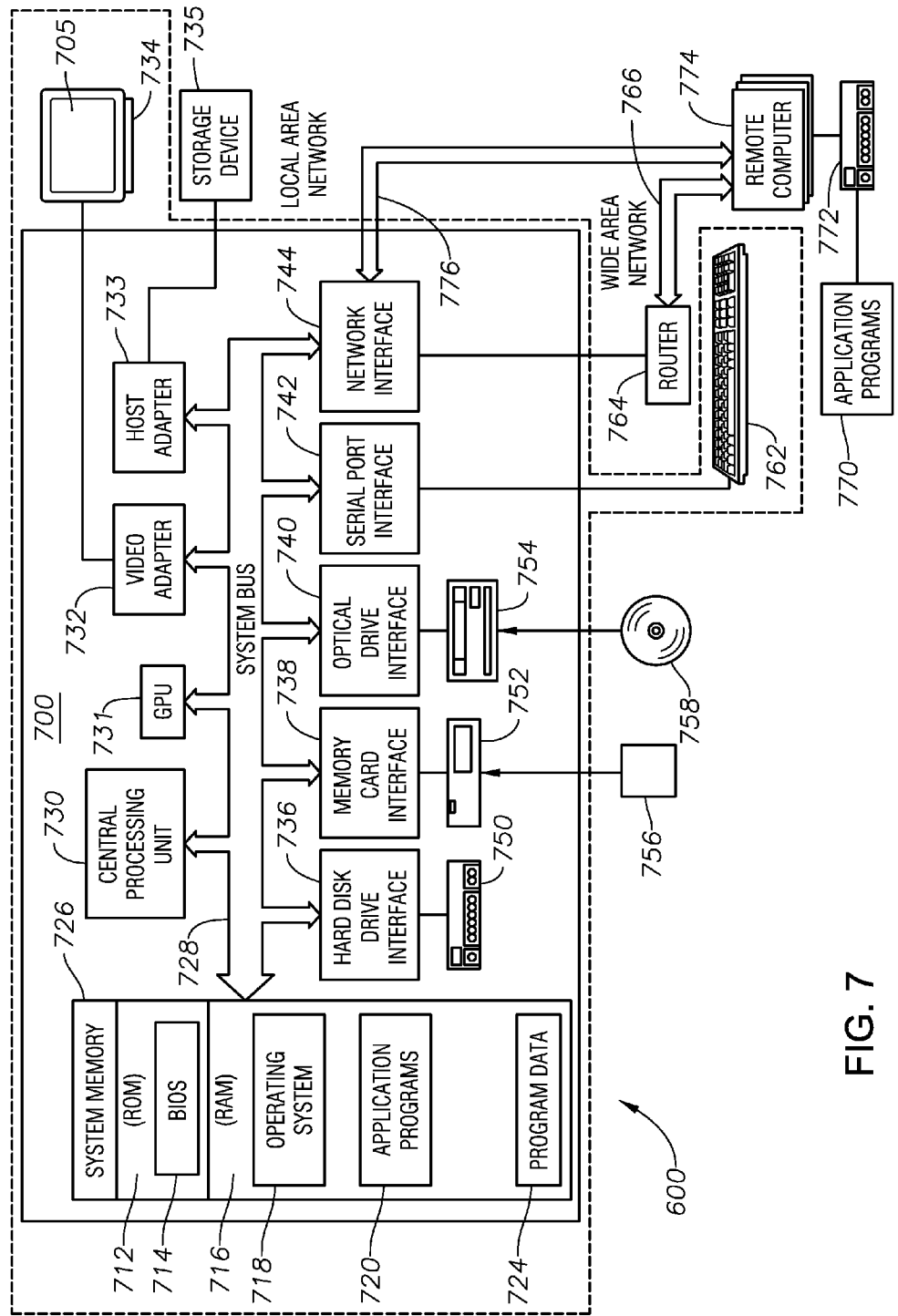
FIG. 7 illustrates a schematic diagram of a video recording system having a computing system in which the various technologies described herein may be incorporated and practiced.
Figure 8:
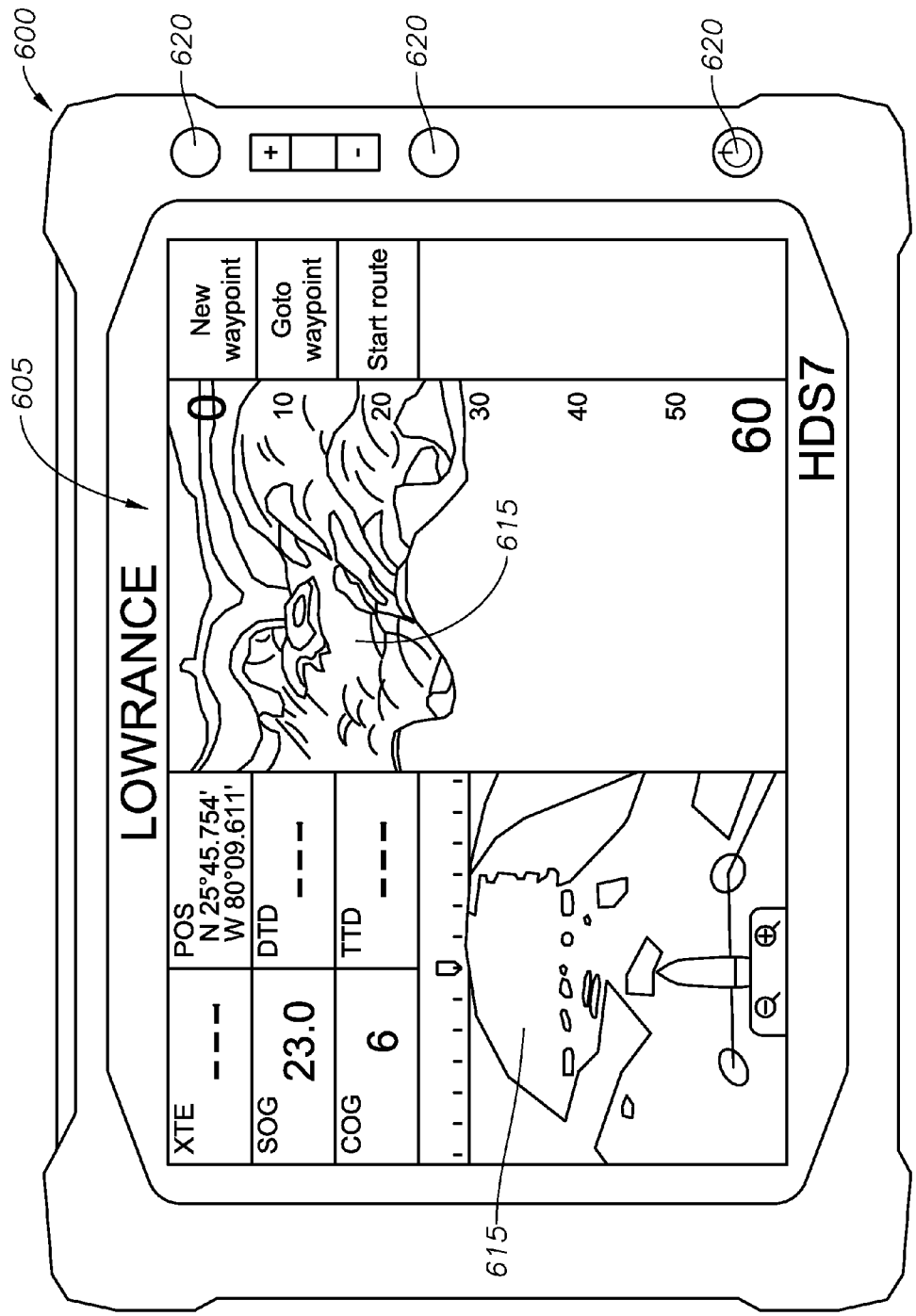
FIG. 8 illustrates a schematic of a marine electronics device in accordance with implementations of various techniques described herein.

The computer 330 is described in more detail in FIG. 7. In one implementation, the computer 330 may be loaded with software to analyze motion data from the at least one motion sensor 340. For instance, the software may analyze motion data to determine when a fishing cast motion has been made. The software may also record that a cast has been made and the time of the cast, e.g., a timestamp. The software is described in more detail in FIG. 5.

The wearable device 300 may include one or more buttons 310. The one or more buttons 310 may be used for user input. In one implementation, the one or more buttons 310 may be used to input the occurrence of a cast. In another implementation, the one or more buttons 310 may be used to input the occurrence of a catch. The catch may then be recorded. In another implementation, the one or more buttons 310 may be used to input the weight of a caught fish. The weight may then be recorded. In yet another implementation, a user may press a button 310 to input the occurrence of a catch, and then may press the same or different button 310 to input the weight of the caught fish. The occurrence of the catch and the weight may then be recorded. In still another implementation, the one or more buttons 310 may be used to input the occurrence of a bite.

The wearable device may contain a display 350. The display may be a series of Light Emitting Diodes (LED). The display may be a Liquid Crystal Display (LCD).

The wearable device 300 may include wireless technology, such as Bluetooth, Wi-Fi, cellular technology such as GSM or CDMA, satellite communication, or any other wireless technology. In one implementation, the wearable device 300 may be connected wirelessly to a marine electronics device 600, which is described in more detail in FIG. 8. Although the wearable device 300 is described as being wirelessly connected to a marine electronics device 600, it should be understood that the wearable device 300 may be connected to any computer system, including a portable computer system, a smart phone device, a remote server, the video recorder 110, a cloud server and the like. It should also be understood that the wearable device 300 may be connected to any other device able to store fishing data, e.g., data logging device.

The marine electronics device 600 or a computer system, including a smart phone, may record additional data, such as location, weather, or other data. The data from the marine electronics device 600 or computer system and the wearable device 300 may then be combined to provide comprehensive data regarding a fishing trip. The combined data may then be transmitted directly to a remote server or cloud. In one implementation, the combined data may be transmitted to a smart phone device, which then transmits the data to a remote server or cloud. In another implementation, the combined data may be transmitted to the data logging device, which may then transmit the combined data at a later time. In yet another implementation, the data from the wearable device 300 may be transmitted to the remote server or cloud via the smart phone without using the marine electronics device 600. In still another implementation, the data from the wearable device may be transmitted to a data logging device prior to being transmitted to a remote server or cloud via the smart phone. In still another implementation, the data from the wearable device 300 may be transmitted to the remote server or cloud without using the marine electronics device 600 or the smartphone.

Fishing Motion Detection

Figure 5:
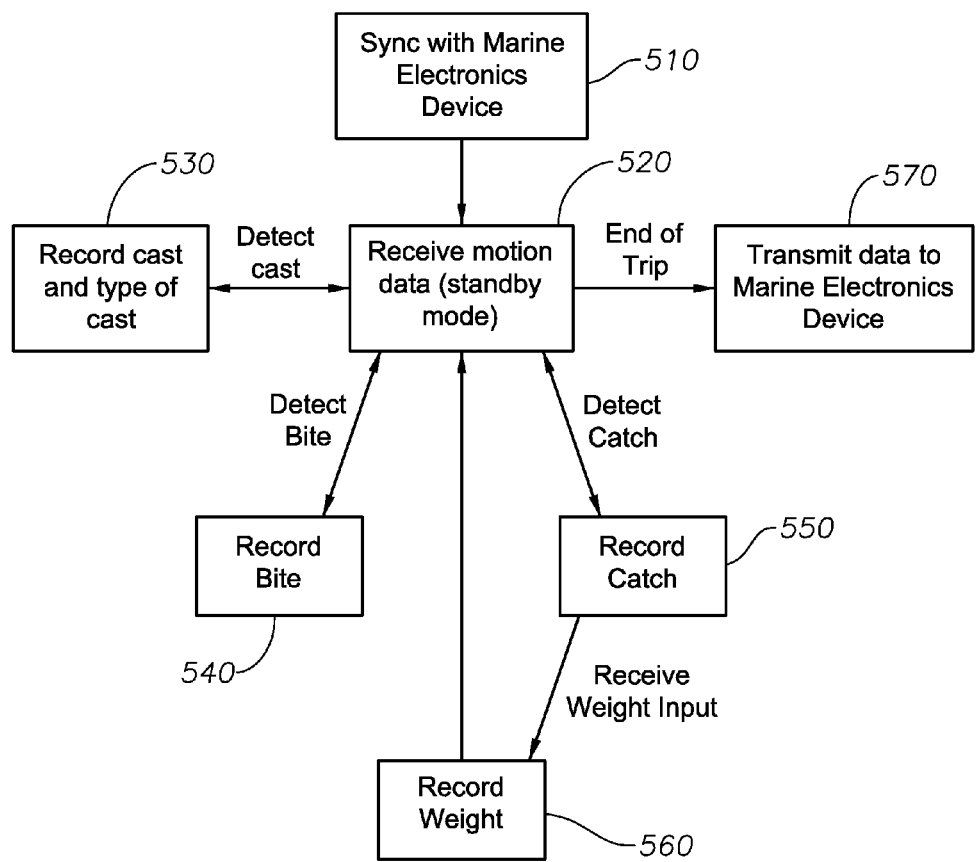
FIG. 5 is a flow diagram describing the operation of a fishing motion detecting software loaded in a wearable device in accordance with implementations of various techniques described herein.

FIG. 5 illustrates a flow diagram of a cast detection method 500 in accordance with implementations of various techniques described herein. In one implementation, method 500 may be performed by the computer 330. It should be understood that while method 500 indicates a particular order of execution of operations, in some implementations, certain portions of the operations might be executed in a different order. Further, in some implementations, additional operations or steps may be added to the method 500. Likewise, some operations or steps may be omitted.

As mentioned above, the computer 330 contained in a wearable device 300 may be loaded with a set of instructions (software) to analyze data received from one or more sensors. The software may receive motion data from the at least one motion sensor 340 in the wearable device. The software may analyze the motion data and determine when a cast has been made. The software may record the occurrence of the cast and time of the cast, e.g., a timestamp in memory, e.g., inside the computer 330. The record may be a database, a log, or any other method of recording the fishing data. The record may be a number representing the amount of casts that have occurred, with the number being incremented after each cast. The amount of casts may be shown on a display 350.

At block 510, the computer 330 may be synchronized to a marine electronics device or a portable computer device, such as a smart phone. This step is optional. In one implementation, the computer 330 may be wirelessly synchronized to the marine electronics device 600. FIG. 7 illustrates the wearable device 300 being synchronized to the marine electronics device.

At block 520, the software may enter a standby mode in which data may be received from the at least one motion sensor 340 and analyzed. At this step, the software may continuously monitor for a cast. Once a cast is detected, the cast and the timestamp corresponding to the detected cast may be recorded (block 550). In one implementation, the software may determine the type of cast used using motion sensor data (block 550). The software may determine whether the cast made is a basic cast, roll cast, side cast, or any other type of cast. The software may then record the type of cast made (block 550). Then, the software returns to the standby mode (block 530).

While in standby mode (block 530), the software may detect a catch or a bite. The software may detect a catch or a bite based on the motion sensor data. Once a bite or a catch is detected, the occurrence of a bite or a catch and their corresponding timestamp may be recorded (block 540/550). The record may be a database, a log, or any other method of recording the fishing data. The record may be a number representing the amount of bites or catch that have occurred, with the number being incremented after each bite or catch. The amount of bites or catch may be shown on a display 350. Then, the software returns to the standby mode (block 520).

In one implementation, casts, bites and/or catches may be detected using one or more buttons 310. To indicate a bite, a user may press a first button 310. To indicate a catch, a user may press a second, different button 310. To indicate a cast, a user may press a third, different button 310. Alternately, a user may press a button 310 and then quickly release the button 330 to indicate the occurrence of a bite. The user may also press the same button 310 and hold the button 310 down for a longer time to indicate a catch.

Once a catch is detected, the software may receive further user input corresponding to the weight of the caught fish (block 560). If the software receives further user input, the software may then record the weight of the caught fish (block 560). The record may be a database, a log, or any other method of recording the fishing data. The inputted weight may be shown on a display 350. Then, the software returns to the standby mode (block 520).

In one implementation, the weight is entered using one or more buttons 310. A weight may be entered by pushing the one or more buttons 310 a number of times to correspond to the weight of the caught fish. For example, to enter a three pound fish, a button 310 may be pressed three times.

When the trip is over, the software may transmit the recorded data wirelessly to the connected device, e.g., the marine electronics device 600 (block 570). In one implementation, the software may transmit the record data after each new entry, or at any other interval. For example, the transmission may be made after each cast. The transmission may be to a remote server or to any computer system, including a smart phone or a marine electronics device.

Marine Electronics Device

Figure 6:
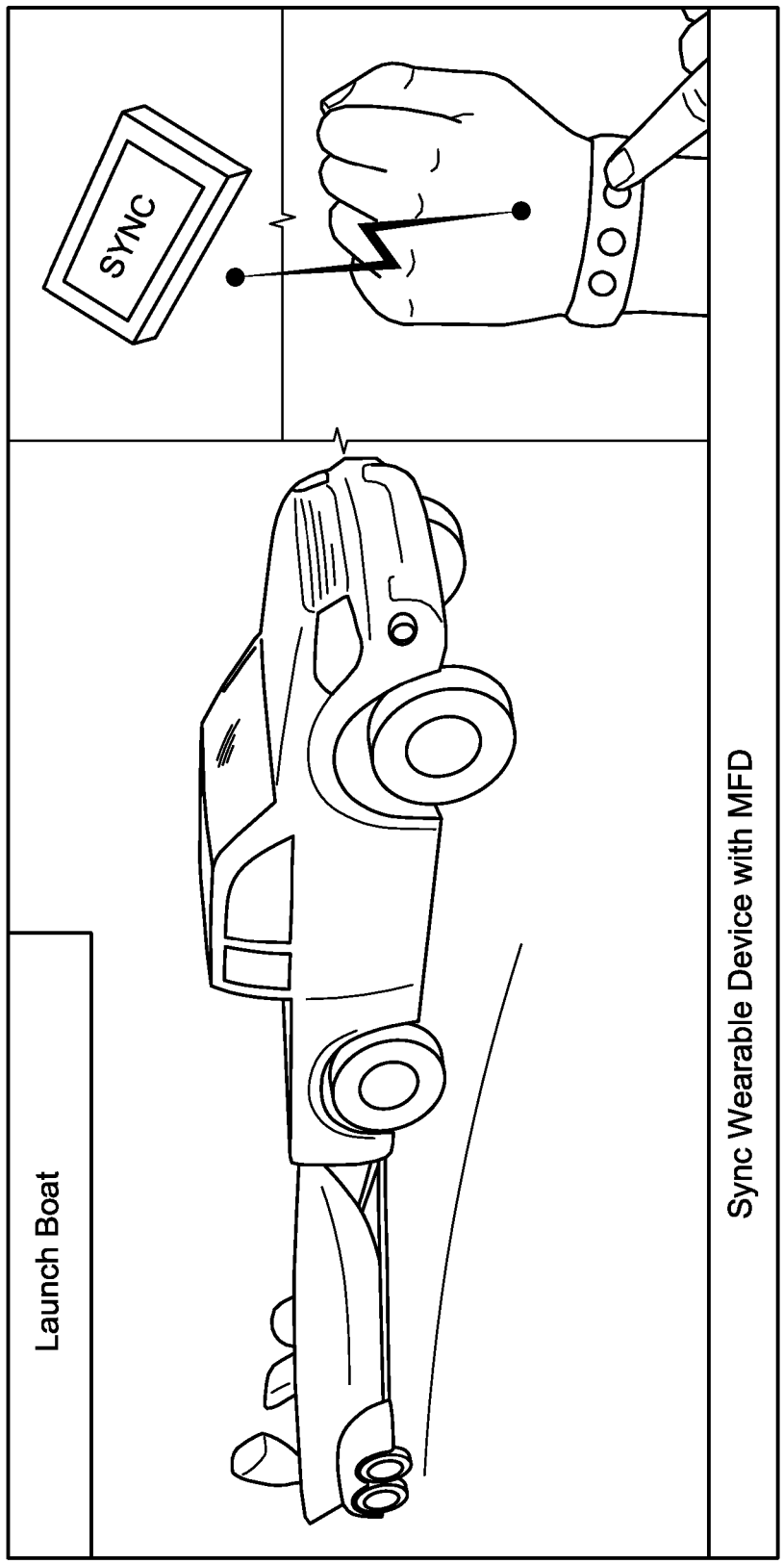
FIG. 6 is an illustration of a wearable device wirelessly transmitting data to a marine electronics device and receiving data from the device in order to begin recording data in accordance with implementations of various techniques described herein.

FIG. 6 illustrates a schematic diagram of a marine electronics device 600 in accordance with various implementations described herein. The components of the marine display device 600 are described in more detail with reference to the computing system 700 in FIG. 7. The marine electronics device 600 includes a screen 605. In certain implementations, the screen 605 may be sensitive to touching by a finger. In other implementations, the screen 605 may be sensitive to the body heat from the finger, a stylus, or responsive to a mouse. The display device 600 may display marine electronic data 615. The marine electronic data types 615 may include chart data, radar data, sonar data, steering data, dashboard data, navigation data, fishing statistics, and the like. The marine electronics device 600 may also include a plurality of buttons 620, which may be either physical buttons or virtual buttons, or a combination thereof.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, and the like.

The various technologies described herein may be implemented in the context of marine electronics, such as devices found in marine vessels and/or navigation systems. Ship instruments and equipment may be connected to the computing systems described herein for executing one or more navigation technologies. As such, the computing systems may be configured to operate using sonar, radar, the global positioning system (GPS) and like technologies.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

FIG. 7 illustrates a schematic diagram of the video recording system 100 having a computing system 700 in accordance with implementations of various techniques described herein. The computer system 700 may describe the video recorder 110, the marine electronics device 600, the wearable device 300, or components spanning multiple devices. The computing system 700 may be a conventional desktop, a handheld device, a controller, a personal digital assistant, a server computer, an electronics device/instrument, a laptop, a tablet, or part of a navigation system, or sonar system. It should be noted, however, that other computer system configurations may be used.

The computing system 700 may include a central processing unit (CPU) 730, a system memory 726, a graphics processing unit (GPU) 731 and a system bus 728 that couples various system components including the system memory 726 to the CPU 730. Although only one CPU 730 is illustrated in FIG. 7, it should be understood that in some implementations the computing system 700 may include more than one CPU 730.

The CPU 730 can include a microprocessor, a microcontroller, a processor, a programmable integrated circuit, or a combination thereof. The CPU 730 can comprise an off-the-shelf processor such as a Reduced Instruction Set Computer (RISC), or a Microprocessor without Interlocked Pipeline Stages (MIPS) processor, or a combination thereof. The CPU 730 may also include a proprietary processor.

The GPU 731 may be a microprocessor specifically designed to manipulate and implement computer graphics. The CPU 730 may offload work to the GPU 731. The GPU 731 may have its own graphics memory, and/or may have access to a portion of the system memory 726. As with the CPU 730, the GPU 731 may include one or more processing units, and each processing unit may include one or more cores.

The CPU 730 may provide output data to a GPU 731. The GPU 731 may generate graphical user interfaces that present the output data. The GPU 731 may also provide objects, such as menus, in the graphical user interface. A user may provide inputs by interacting with the objects. The GPU 731 may receive the inputs from interaction with the objects and provide the inputs to the CPU 730. A video adapter 732 may be provided to convert graphical data into signals for a monitor 734. The monitor 734 includes a screen 705. The screen 705 can be sensitive to heat or touching (now collectively referred to as a "touch screen"). In one implementation, the host computer 799 may not include a monitor 734.

The system bus 728 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 726 may include a read only memory (ROM) 712 and a random access memory (RAM) 716. A basic input/output system (BIOS) 714, containing the basic routines that help transfer information between elements within the computing system 700, such as during start-up, may be stored in the ROM 712.

The computing system 700 may further include a hard disk drive interface 736 for reading from and writing to a hard disk 750, a memory card reader 752 for reading from and writing to a removable memory card 756, and an optical disk drive 754 for reading from and writing to a removable optical disk 758, such as a CD ROM or other optical media. The hard disk 750, the memory card reader 752, and the optical disk drive 754 may be connected to the system bus 728 by a hard disk drive interface 736, a memory card reader interface 738, and an optical drive interface 740, respectively. The drives and their associated computer-readable media may provide nonvolatile storage of computer-readable instructions, data structures, program modules and other data for the computing system 700.

Although the computing system 700 is described herein as having a hard disk, a removable memory card 756 and a removable optical disk 758, it should be appreciated by those skilled in the art that the computing system 700 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the computing system 700. Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The computing system 700 may also include a host adapter 733 that connects to a storage device 735 via a small computer system interface (SCSI) bus, a Fiber Channel bus, an eSATA bus, or using any other applicable computer bus interface. The computing system 700 can also be connected to a router 764 to establish a wide area network (WAN) 766 with one or more remote computers 774. The router 764 may be connected to the system bus 728 via a network interface 744. The remote computers 774 can also include hard disks 772 that store application programs 770.

In another implementation, as discussed in more detail with respect to FIG. 2, the computing system 700 may also connect to one or more remote computers 774 via local area network (LAN) 776 or the WAN 766. When using a LAN networking environment, the computing system 700 may be connected to the LAN 776 through the network interface or adapter 744. The LAN 776 may be implemented via a wired connection or a wireless connection. The LAN 776 may be implemented using Wi-Fi technology, cellular technology, or any other implementation known to those skilled in the art. The network interface 744 may also utilize remote access technologies (e.g., Remote Access Service (RAS), Virtual Private Networking (VPN), Secure Socket Layer (SSL), Layer 2 Tunneling (L2T), or any other suitable protocol). These remote access technologies may be implemented in connection with the remote computers 774. It will be appreciated that the network connections shown are exemplary and other means of establishing a communications link between the computer systems may be used.

A number of program modules may be stored on the hard disk 750, memory card 756, optical disk 758, ROM 712 or RAM 716, including an operating system 718, one or more application programs 720, and program data 724. In certain implementations, the hard disk 750 may store a database system. The database system could include, for example, recorded points. The application programs 720 may include various mobile applications ("apps") and other applications configured to perform various methods and techniques described herein. The operating system 718 may be any suitable operating system that may control the operation of a networked personal or server computer.

A user may enter commands and information into the computing system 700 through input devices such as a keyboard 762 and pointing device. Other input devices may include a microphone, joystick, game pad, satellite dish, scanner, user input button, or the like. These and other input devices may be connected to the CPU 730 through a serial port interface 742 coupled to system bus 523, but may be connected by other interfaces, such as a parallel port, game port or a universal serial bus (USB). A monitor 105 or other type of display device may also be connected to system bus 728 via an interface, such as a video adapter 732. In addition to the monitor 734, the computing system 700 may further include other peripheral output devices such as speakers and printers.

While the foregoing is directed to implementations of various techniques described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A non-transitory computer-readable medium having stored thereon a plurality of computer-executable instructions which, when executed by a computer, cause the computer to:
   receive, from a wearable device, a first cast notification that a first cast has been made, wherein the wearable device includes one or more motion sensors that are not connected to a fishing line, wherein the wearable device determines that the first cast has been made based on first motion data from the one or more sensors, and wherein the first motion data corresponds to a user of the wearable device initiating the first cast;
   receive video data corresponding to fishing activity;
   delete, in an instance in which a second cast notification that a second cast has been made is received from the wearable device, at least a portion of the video data associated with the first cast, wherein the wearable device determines that the second cast has been made based on second motion data from the one or more sensors, and wherein the second motion data corresponds to the user of the wearable device initiating the second cast; and
   store, in an instance in which a notification that a catch or bite has occurred is received from the wearable device, at least the portion of the video data associated with the first cast in memory, wherein the wearable device determines that the catch or bite has occurred based on third motion data from the one or more sensors, and wherein the third motion data corresponds to an instance in which the user of the wearable device has a catch or a bite.

2. The non-transitory computer-readable medium of claim 1, wherein the at least a portion of the data is deleted without deleting video data associated with the second cast.

3. The non-transitory computer-readable medium of claim 1, wherein the computer-executable instructions further cause the computer to:
   receive a first time stamp corresponding to the first cast;
   receive a second time stamp corresponding to the second cast; and
   determine the portion of the video data to delete to be between the first time stamp and the second time stamp.

4. The non-transitory computer-readable medium of claim 3, wherein the computer-executable instructions further cause the computer to determine the ending of the portion of the video data to delete to be a staggered point in time prior to the second time stamp so as to not inadvertently delete any portion of the second cast.

5. The non-transitory computer-readable medium of claim 1, wherein the computer-executable instructions further cause the computer to associate the portion of the video data to be stored with at least one of the first cast or the catch or bite in the memory.

6. The non-transitory computer-readable medium of claim 1, wherein the video data is recorded by a video camera located remotely from the wearable device.

7. The non-transitory computer-readable medium of claim 1, wherein the first cast notification, the second cast notification, and the notification that the catch or bite has occurred are each received over a wireless connection.

8. The non-transitory computer-readable medium of claim 1, wherein the computer-executable instructions further cause the computer to:
   receive, from the wearable device, a record of a type of fishing cast made by the user for the first cast, wherein the wearable device determines the type of fishing cast based on the first motion data, wherein the type of fishing cast includes at least one of a basic fishing cast, a roll fishing cast, or a side fishing cast; and
   store the record of the type of fishing cast in association with the portion of the video data associated with the first cast.

9. The non-transitory computer-readable medium of claim 1, wherein the video data corresponding to the fishing activity shows a user of the wearable device during the fishing activity.

10. A marine electronics device comprising:
one or more processors; and
memory having stored thereon a plurality of executable instructions which, when executed by the one or more processors, cause the one or more processors to:
receive, from a wearable device, a first cast notification that a first cast has been made, wherein the wearable device includes one or more motion sensors that are not connected to a fishing line, wherein the wearable device determines that the first cast has been made based on first motion data from the one or more sensors, and wherein the first motion data corresponds to a user of the wearable device initiating the first cast;
receive video data corresponding to fishing activity;
delete, in an instance in which a second cast notification that a second cast has been made is received from the wearable device, at least a portion of the video data associated with the first cast, wherein the wearable device determines that the second cast has been made based on second motion data from the one or more sensors, and wherein the second motion data corresponds to the user of the wearable device initiating the second cast; and
store, in an instance in which a notification that a catch or bite has occurred is received from the wearable device, at least the portion of the video data associated with the first cast in the memory, wherein the wearable device determines that the catch or bite has occurred based on third motion data from the one or more sensors, and wherein the third motion data corresponds to an instance in which the user of the wearable device has a catch or a bite.

11. The marine electronics device of claim 10, wherein the plurality of executable instructions are further configured to cause the one or more processors to:
receive a first time stamp corresponding to the first cast;
receive a second time stamp corresponding to the second cast; and
determine the portion of the video data to delete to be between the first time stamp and the second time stamp.

12. The marine electronics device of claim 10, wherein the plurality of executable instructions are further configured to cause the one or more processors to associate the portion of the video data to be stored with at least one of the first cast or the catch or bite in the memory.

13. The marine electronics device of claim 10, wherein the video data is recorded by a video camera located remotely from the wearable device.

14. The marine electronics device of claim 10, wherein the first cast notification, the second cast notification, and the notification that the catch or bite has occurred are each received over a wireless connection.

15. The marine electronics device of claim 10, wherein the plurality of executable instructions are further configured to cause the one or more processors to:
receive, via the wearable device, a record of a type of fishing cast made by the user for the first cast, wherein the wearable device determines the type of fishing cast based on the first motion data, wherein the type of fishing cast includes at least one of a basic fishing cast, a roll fishing cast, or a side fishing cast; and
store the record of the type of fishing cast in association with the portion of the video data associated with the first cast.

16. The marine electronics device of claim 10, wherein the video data corresponding to the fishing activity shows a user of the wearable device during the fishing activity.

17. A system comprising:
a wearable device comprising:
one or more motion sensors, wherein the one or more motion sensors are not connected to a fishing line; and
a computer system having a wearable device processor and memory having stored thereon a plurality of executable instructions which, when executed by the wearable device processor of the wearable device, cause the wearable device processor to:
receive first motion data from the one or more motion sensors, wherein the first motion data corresponds to a user of the wearable device initiating a first cast;
determine, based on the first motion data, that the first cast has been made;
cause, in response to determining that the first cast has been made, transmission of a first cast notification to a marine electronics device;
receive second motion data from the one or more motion sensors, wherein the second motion data corresponds to the user of the wearable device initiating a second cast;
determine, based on the second motion data, that the second cast has been made;
cause, in response to determining that the second cast has been made, transmission of a second cast notification to the marine electronics device;
receive third motion data from the one or more motion sensors, wherein the third motion data corresponds to an instance in which the user of the wearable device has a catch or a bite;
determine, based on the third motion data, that the catch or the bite has occurred; and
cause, in response to determining that the catch or the bite has occurred, transmission of a notification that the catch or bite has occurred to the marine electronics device; and
the marine electronics device, wherein the marine electronics device comprises a marine electronics device processor and memory having stored thereon a plurality of executable instructions which, when executed by the marine electronics device processor of the marine electronics device, cause the marine electronics device processor to:
receive, from the wearable device, the first cast notification that the first cast has been made;
receive video data corresponding to fishing activity;
delete, in an instance in which the second cast notification that the second cast has been made is received from the wearable device, at least a portion of the video data associated with the first cast; and
store, in an instance in which the notification that the catch or bite has occurred is received from the wearable device, at least the portion of the video data associated with the first cast in the memory.

18. The system of claim 17, wherein the plurality of executable instructions of the marine electronics device are further configured to cause the marine electronics device processor to:
receive a first time stamp corresponding to the first cast;
receive a second time stamp corresponding to the second cast; and determine the portion of the video data to delete to be between the first time stamp and the second time stamp.

19. The system of claim 17 further comprising a video camera remotely located from the wearable device and configured to generate the video data.

20. The system of claim 17, wherein the plurality of executable instructions of the marine electronics device are further configured to cause the marine electronics device processor to:
  receive, from the wearable device, a record of a type of fishing cast made by the user for the first cast, wherein the wearable device determines the type of fishing cast based on the first motion data, wherein the type of fishing cast includes at least one of a basic fishing cast, a roll fishing cast, or a side fishing cast; and
  store the record of the type of fishing cast in association with the portion of the video data associated with the first cast.

* * * * *